United States Patent [19]
Mattson et al.

[11] Patent Number: 5,638,737
[45] Date of Patent: Jun. 17, 1997

[54] SPLINE PUMPING ASSEMBLY

[75] Inventors: Andrew P. Mattson; Martyn Abbott, both of Richardson; Lee K. Kulle, Plano, all of Tex.

[73] Assignee: Quest Medical, Inc., Allen, Tex.

[21] Appl. No.: 563,202

[22] Filed: Nov. 27, 1995

[51] Int. Cl.$^6$ ............................................. F16J 3/02
[52] U.S. Cl. ........................... 92/101; 92/90; 92/93
[58] Field of Search ......................... 92/90, 91, 92, 92/93, 96, 98 R, 101, 104

[56] References Cited

U.S. PATENT DOCUMENTS

| | | | |
|---|---|---|---|
| 1,637,219 | 7/1927 | Edelmann | 92/92 |
| 3,204,568 | 9/1965 | Grossfield | 92/104 X |
| 4,270,441 | 6/1981 | Tuck, Jr. | 92/98 R X |
| 4,375,182 | 3/1983 | Zavoda | 92/98 R |
| 4,391,600 | 7/1983 | Archibald . | |
| 4,657,490 | 4/1987 | Abbott . | |
| 5,054,373 | 10/1991 | Brault et al. | 92/92 |
| 5,060,539 | 10/1991 | Cissell et al. | 92/92 X |
| 5,115,724 | 5/1992 | Zavoda | 91/102 |
| 5,335,584 | 8/1994 | Bair | 92/98 R |
| 5,349,896 | 9/1994 | Delanay, III et al. | 92/98 R |

*Primary Examiner*—F. Daniel Lopez
*Attorney, Agent, or Firm*—Steven P. Rhines, Quest Medical, Inc.

[57] ABSTRACT

The present invention relates to a piston assembly for use in a fluid delivery system. The piston assembly is comprised of two elements: a splined-piston having generally a convex shape and a ribbed-base, that receives the piston, which has a complementary concave shape. The interposition of the splines and ribs and the complementary shaping of the two elements permit: a constant supporting surface area to be realized throughout a pumping cycle; the establishment of a constant supporting surface that readily and fully supports a thin, flexible material such that the material cannot not likely become stretched, unsupported or bound within the pumping mechanism throughout the pumping cycle; and the establishment of a relationship between the piston and its associated pumping chamber that enables a precise volumetric quantity to be delivered consistently and accurately.

20 Claims, 7 Drawing Sheets

SPLINE PUMPING ASSEMBLY

BACKGROUND OF THE INVENTION

1. Field of the Invention

The invention relates to a piston assembly, and more particularly to a piston assembly for a pump mechanism that delivers a sterile fluid for medical treatment.

2. Description of Related Art

The pressurized delivery of fluids to a patient involves numerous challenges and concerns. Doctors and perfusionist often face issues relating to: delivery of a precise volumetric flow or a precise ratio of two fluids; preserving the sterility of the fluid throughout the fluid's journey through the pumping mechanism; and, if the fluid is blood or a blood-fluid mixture, the infusion of damaged blood, such damage occurring through the features inherent to the most widely used pumping systems.

A variety of systems exist for the purpose of pumping fluids for medical infusion. Two of the more widely used classes of fluid pumps include roller pumps and centrifugal pumps. A roller pump uses a rotating, variably-occlusive roller to systematically push fluid through tubing by compressing the tubing against a track that partially surrounds the rotating roller. A centrifugal pump possess a turbine, to which the fluid being pumped must come in contact, that pushes the fluid along a fluid path. Both pumps possess distinct features that can damage blood or the blood constituent of a blood-fluid mixture. Hemolysis, or the physical destruction of red blood cells, can occur through either the compressive forces applied by the roller of the roller pump, or the shear forces created by the turbine of the centrifugal pump. Moreover, neither of these pump systems provide a means for delivering consistent, precise volumetric quantities or allowing the consistent mixture of multiple fluids in precise ratios. Other pumping means which exist, but are not as prevalent as the aforementioned, include a "rolling diaphragm," as disclosed in U.S. Pat. No. 4,391,600 (Archibald), and a "petal assembly," as disclosed in U.S. Pat. 4,657,490 (Abbott).

U.S. Pat. No. 4,391,600 discloses a non-pulsating I.V. pump that receives a disposable fluid cassette. The '600 Patent features cylindrical pump chambers that accommodate cylindrical pistons, such pistons having an outer diameter that is less than the inner diameter of the pump chambers. The fluid cassette possesses cylindrical pumping chambers that fit within the pump's chambers. During operation, the cylindrical chambers of the disposable fluid cassette must "rolls" over itself within the space between the piston and the pump chamber as the piston advances. The result of such rolling is (i) the continuous inducement of varying stresses at the supported-unsupported interface of the cassette; (ii) fluid and/or air may be trapped in the unsupported portion of the cassette during the advancement of the piston, such compromising the volumetric accuracy of the expelled fluid; and (iii) the flexible material of the cassette is required to be pinched and worked throughout the fluid delivery procedure. Importantly, the first and third of these can act on material imperfections or forming imperfections to compromise the integrity of the disposable fluid cassette.

U.S. Pat. No. 4,657,490 discloses an infusion pump that also uses a disposable cassette. The '490 infusion pump features a petal assembly which acts on the cassette. Specifically, the petal assembly includes a central hub surrounded by a plurality of rigid, petal shaped sections. Each petal section spans between the central hub and the fixed housing with surrounds the petal assembly. In operation, the petals form a movable pressing surface. As may be understood, the stroke of the petal assembly is limited by the motion of the petals. Notwithstanding, the shallow angles inherent to the petal assembly are necessary to maintain a constant surface area to support the cassette. As a consequence, however, the shallow petal angles limit the petal assembly's volumetric pumping capacity. Nevertheless, if the petal assembly was altered to move away from the concept of providing a constant supporting surface, the petal assembly becomes incapable of ensuring volumetric accuracy as the resulting pumping chamber would likely facilitate trapped fluids and/or air.

In light of present pumping methods, a need remains for a simple piston assembly that allows for the safe displacement of a relatively significant volume of fluid while also being capable of maintaining consistent volumetric accuracy. Further, such piston assembly should facilitate use of a disposable fluid cassette, wherein the piston assembly provides a constant supporting surface area throughout the pumping motion to prevent damage to the cassette by stretching or allowing the cassette to become pinched or bound during the operation.

SUMMARY OF THE INVENTION

The present invention is directed to a piston assembly and its method of use. According to one embodiment of the present invention, a piston assembly is disclosed that includes a piston and a base. The piston includes a central hub with a plurality of splines extending radially outward therefrom. The piston generally forms a convex shape. The base includes a collar with a plurality of ribs that extend radially inward, such ribs uniformly terminating to define a central passageway which axially extends through the base. The plurality of ribs inversely complement the convex shape of the piston, wherein the ribs generally form a concave shape. The central passageway of the base operatively receives the hub of the piston. Likewise, when operatively engaged, the plurality of splines are movably interposed between the plurality of ribs.

An object of the present invention is to create a repeatable relationship between the pumping motion of the piston assembly and the fluid expelled, such permitting the achievement of accurate volumetric fluid displacement.

Another object of the present invention is to provide a pumping assembly which inherently minimizes the potential for damage to red blood cells.

Another object of the present invention is to establish a piston assembly that utilizes a minimum number of components to enhance reliability.

Another object of the present invention is to accommodate single pumping stroke applications by expelling substantially all the fluid from the pump chamber to which the pump assembly is associated in a single stroke.

Another object of the present invention is to provide a piston assembly to which fluid displacement is volumetric, such that displaced fluid bears a defined relation to the quantified movement of the piston.

Another object of the present invention is to provide a variable support surface that provides (i) a substantially constant support surface area and (ii) does not permit the material of a supported disposable fluid cassette to be stretched, unsupported or pinched between the elements of the piston assembly, throughout a repeated pumping motion. Other objects and advantages of the present invention will be apparent to those of ordinary skill in the art having reference to the following specification together with the drawings.

BRIEF DESCRIPTION OF THE DRAWINGS

Referring now to the drawings in which like reference numerals and letters indicate corresponding element throughout the several views.

DETAILED DESCRIPTION OF THE PREFERRED EMBODIMENTS

Figure 1:
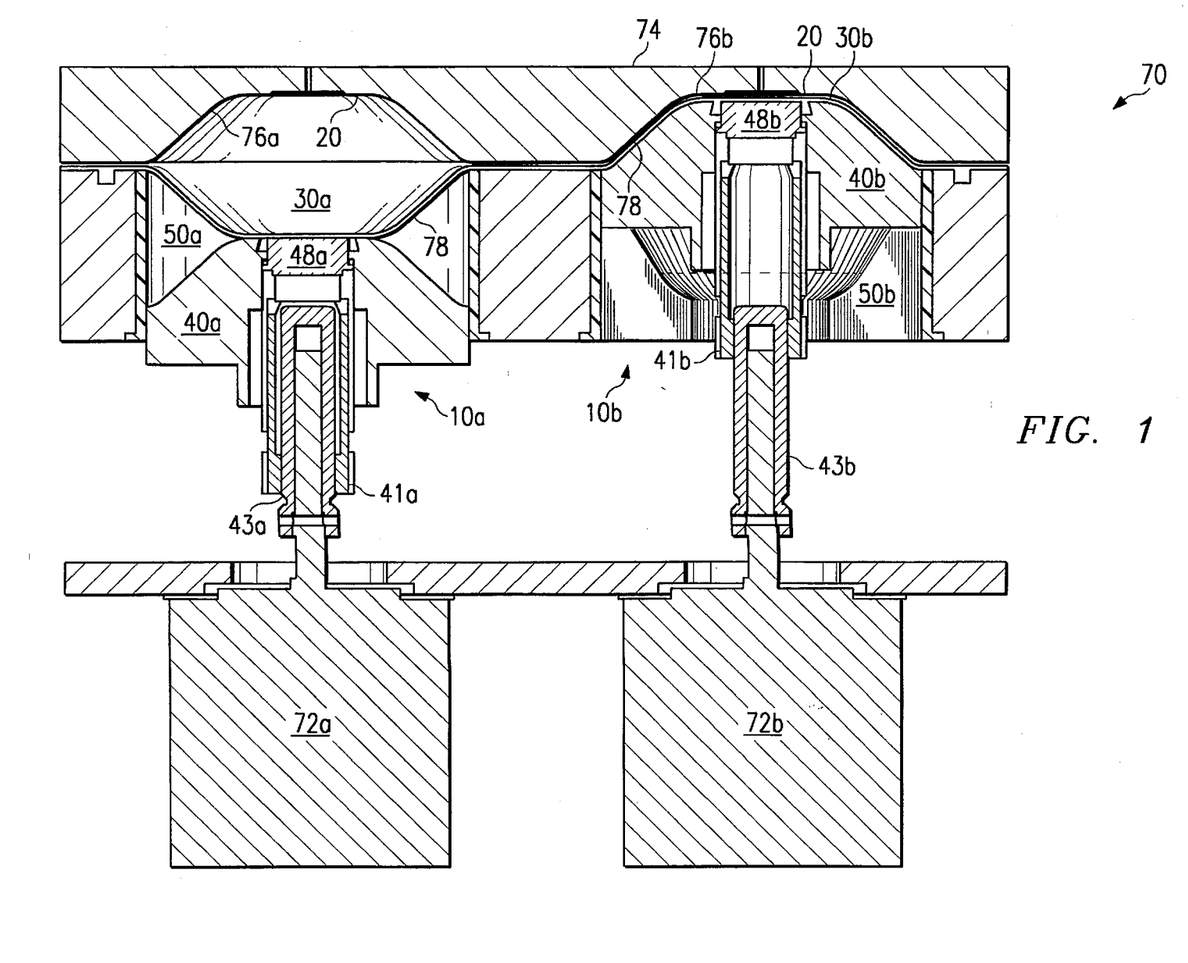
FIG. 1 is a schematic illustration of the functioning of one embodiment of a pump mechanism.

FIG. 1 illustrates one embodiment of a pump mechanism 70 for incorporation into a fluid delivery system (not shown). The pump mechanism 70 operates on a flexible, disposable fluid cassette 20 which maintains the sterility of the fluid as it passes through the mechanism. The pump mechanism 70, as described herein, features two piston assemblies 10a, 10b. The piston assembly 10 of the present invention enables the mixing of multiple fluids in consistent, accurate ratios, and the delivery of such mixture at a definable, consistent volumetric flow rate. A fluid delivery system incorporating the present invention may have multiple applications within the medical industry and, in particular, applications in at least the areas of intravenous fluid delivery, limb perfusion and cardioplegia delivery. Notwithstanding the foregoing, the present invention is adaptable to be incorporated into any variety of fluid delivery systems, whether medical related or not, and scalable to provide a limitless range of volumetric flow rates.

Figure 2:
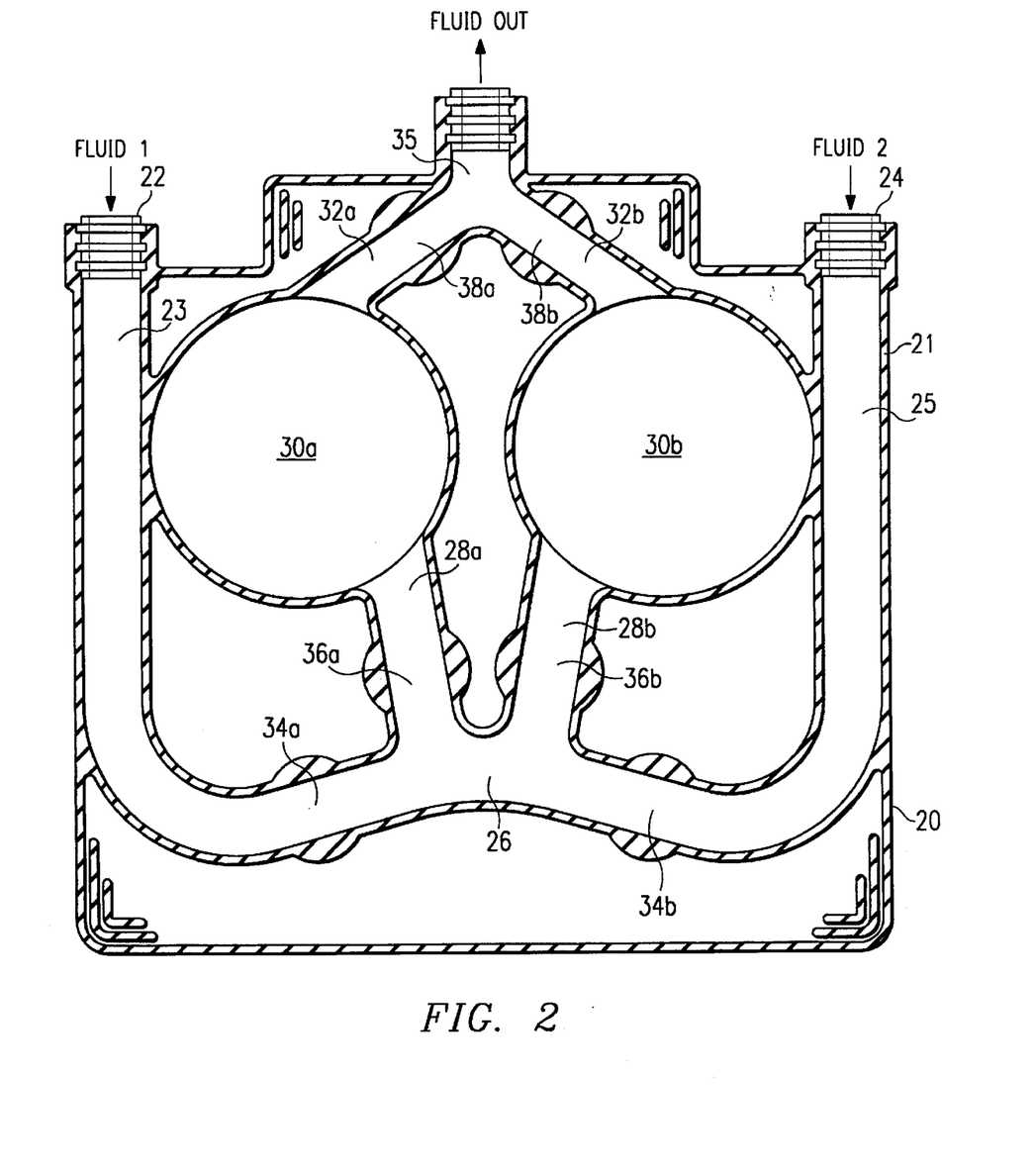
FIG. 2 is a plan view of one embodiment of a disposable fluid cassette for the pump mechanism of FIG. 1.

FIG. 2 illustrates one embodiment of a disposable fluid cassette 20. The cassette 20 may be formed from two thin, flexible sheets of material, such as polyvinylchloride. The sheets are bonded together along a selected bond area 21 to form particularized open flow paths and chambers. Any number of techniques (as an example, RF welding) may be employed for such bonding. The thickness of the material should be such that variations which occur during manufacture should not significantly effect the volumetric accuracy of the fluid output of pump mechanism 70.

The cassette 20 includes a first fluid inlet 22 and a second fluid inlet 24. In a preferred embodiment, the first fluid inlet 22 accommodates blood and the second fluid inlet accommodates a crystalloid fluid typically used during open heart surgery. Fluid entry paths 23, 25 run respectively from inlets 22, 24 to a common inlet path 26, which bifurcates to form inlet flow paths 28a and 28b. Inlet flow paths 28a and 28b respectively terminate in pump chambers 30a, 30b.

Outlet paths 32a, 32b, forming the respective output pathways from pump chambers 30a, 30b, join at a common outlet path 35. The outlet path 35 is the gateway for passage of the first and second fluid mixture to other portions of the fluid delivery system.

Figure 3:
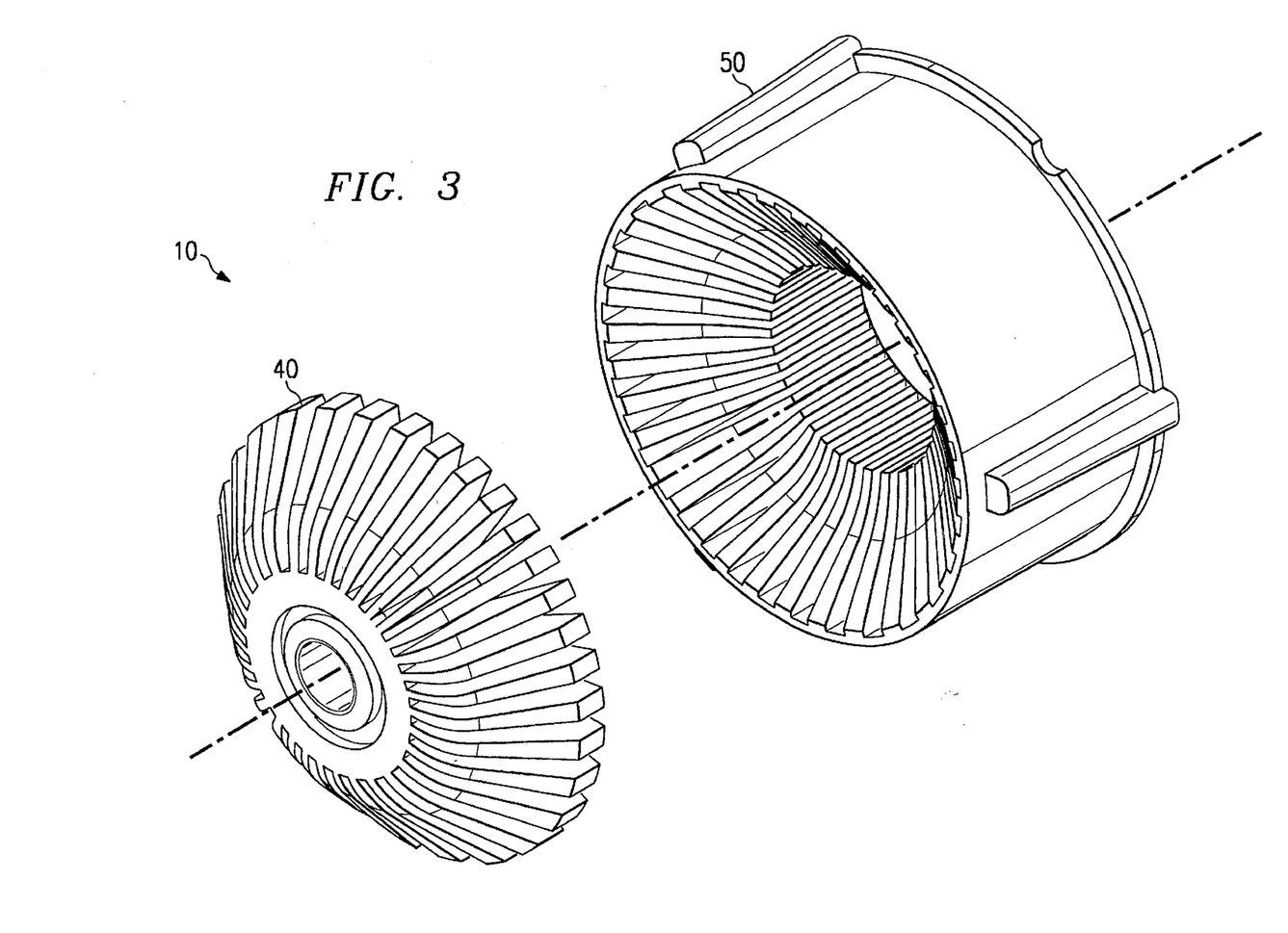
FIG. 3 is an exploded, perspective view of a piston assembly.

FIG. 3 illustrates the piston assembly 10 of FIG. 1. The piston assembly 10 has a piston 40 and a base 50, such base 50 being dimensioned to operatively receiving the piston 40. From FIGS. 4 and 5, piston 40 includes a central hub 42 with a plurality of splines 44 extending outwardly therefrom. The plurality of splines 44 are integrally formed with the hub 42 and extend radially outward. The piston 40 generally forms a convex supporting surface 47, wherein each spline 44 progresses from a full height at the hub 42 to a substantially lesser height at the perimeter of the piston 40. For the preferred embodiment, the angular displacement of the supporting surface 47 corresponds, although in a differing direction of displacement, to an angular displacement of a facial surface, or receiving surface 58, of the base 50.

Figure 4:
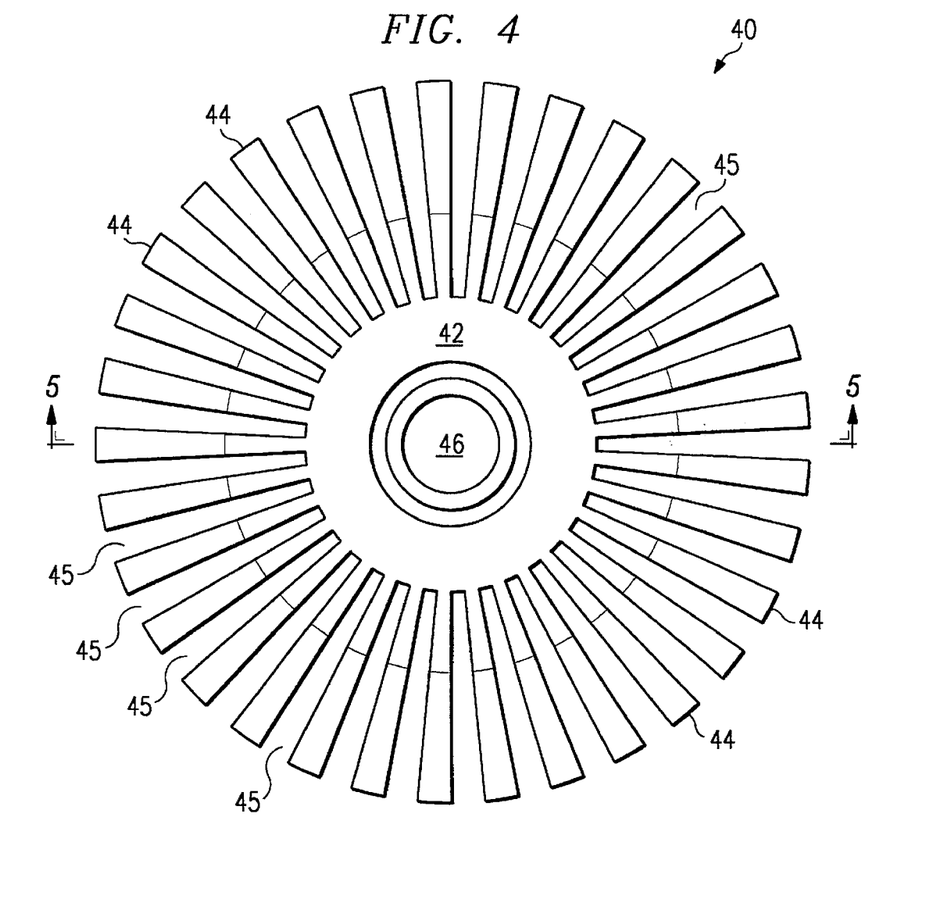
FIG. 4 is a plan view of the piston of the piston assembly of FIG. 3.
Figure 5:
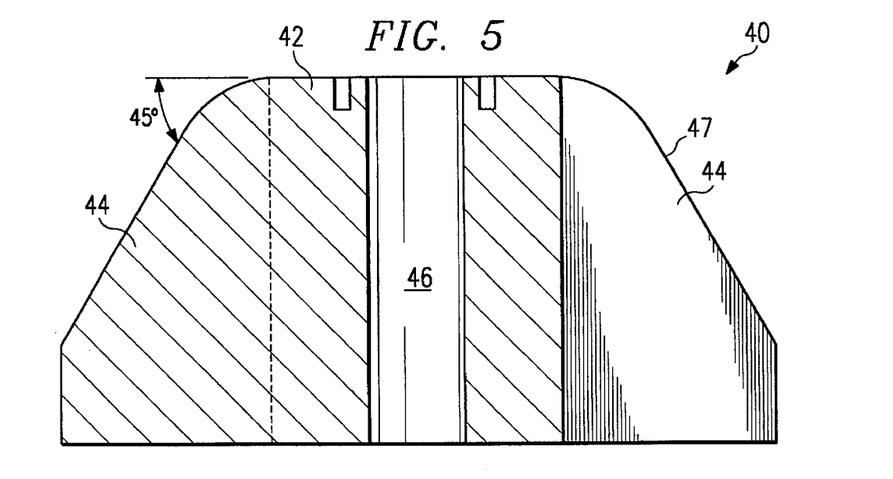
FIG. 5 is a sectional view of the piston along line 5—5 of FIG. 4.
Figure 9:
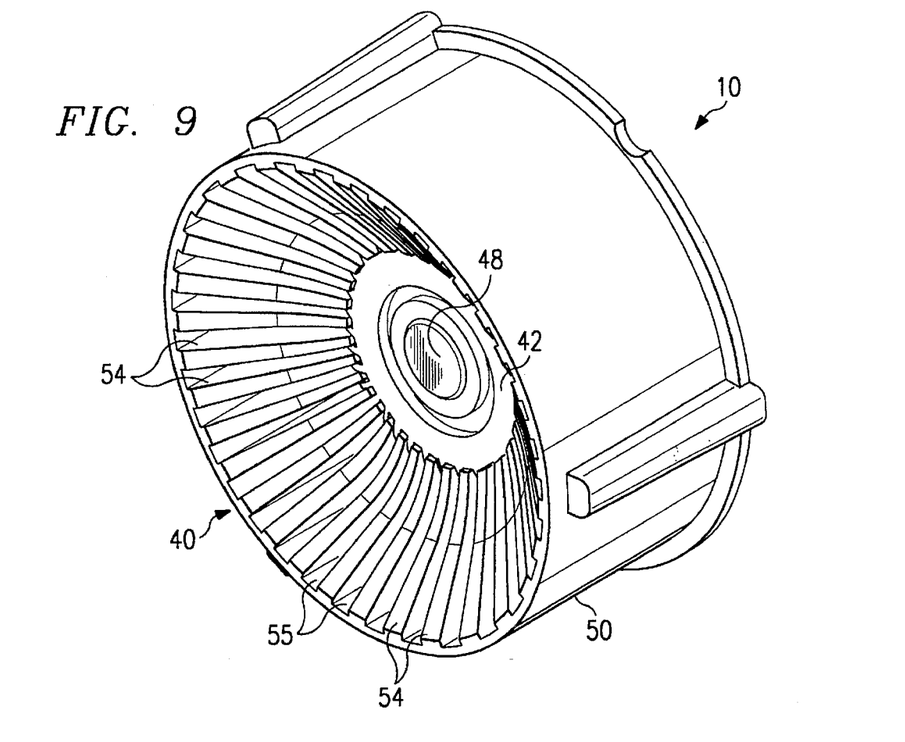
FIG. 9 is a perspective view of the piston assembly in a fully retracted state.

As shown in FIG. 4, the hub 42 can include a passage 46 extending through the piston 40, such passage 46 extending along an axial centerline of the piston 40. In the preferred embodiment, the passage 46 receives and carries a contact pressure sensor 48 (see FIGS. 9 and 10). The incorporation of a pressure sensor 48 in the piston 40 permits monitoring of a fluid pressure within a pumping chamber associated with piston 40. Consequently, the intrachamber fluid pressure is useful in determining: (i) the volumetric content of pumping chamber 30, (ii) the presence of non-occluding valves about pump chamber 30 and (iii) the presence of excessive fluid delivery pressures as well as excessive back-pressures presented to pump mechanism 70.

Figure 6:
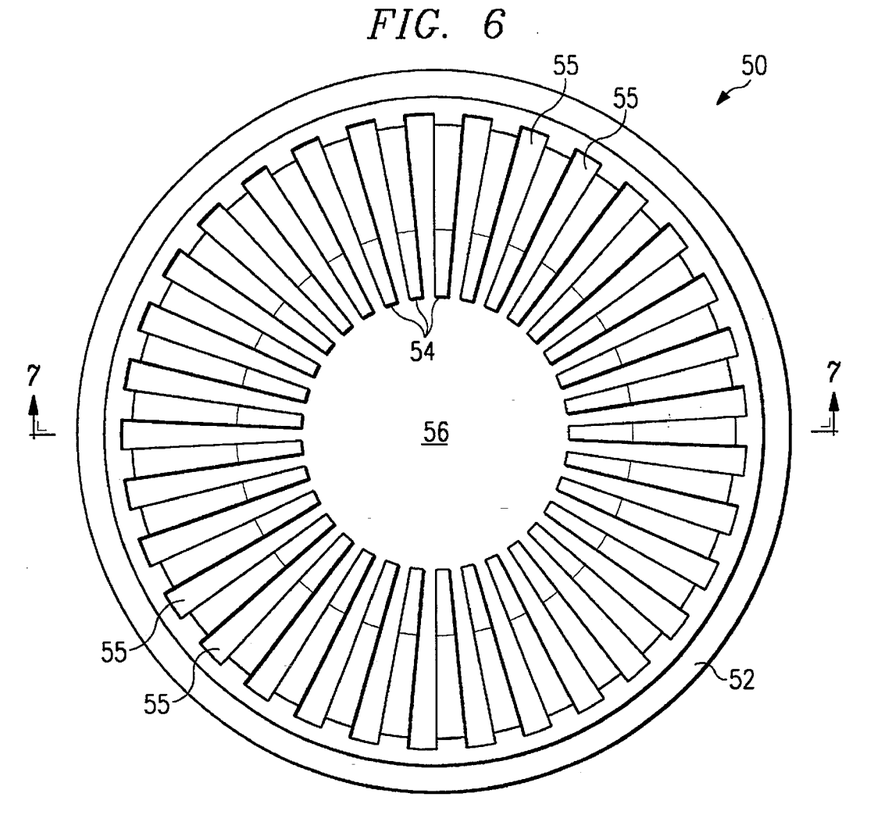
FIG. 6 is a plan view of the base of the piston assembly of FIG. 3.
Figure 7:
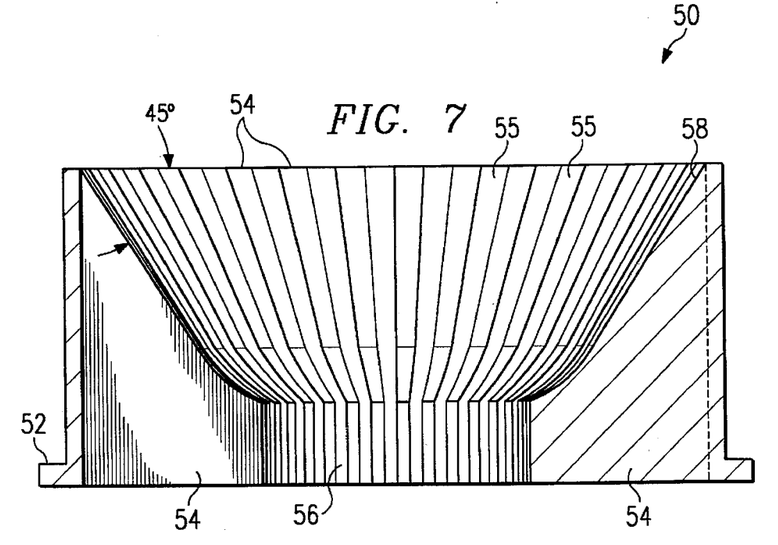
FIG. 7 is a sectional view of the base along line 7—7 of FIG. 6.

As shown in FIGS. 6 and 7, the base 50 includes a collar 52 and a plurality of ribs 54. The plurality of ribs 54 are integrally formed with collar 52 and extend radially inward to define a central passageway 56. The base 50 is constructed so as to (i) permit the hub 42 to be movably received by the central passageway 56 and (ii) allow the plurality of splines 44 to be movably interposed between the plurality of ribs 54 (see FIGS. 9 and 10). As shown in FIG. 7, the ribs 54 generally form a concave receiving surface 58 which inversely complements the convex supporting surface 47 of the piston 40. Accordingly, each rib 54 progresses from a full height at the collar 52 to a substantially lesser height at the perimeter of central passageway 56. In the preferred embodiment, the angular displacement of the receiving surface 58 is substantially 45 degrees, wherein the angular displacement of the supporting surface 47 of the piston 40 is substantially equivalent.

In the preferred embodiment, each spline 44 has a thickness substantially equal to that of each rib 54. Therefore, when the base 50 receives the piston 40 there exists limited and tightly controlled clearance between any rib-spline interface, thereby preventing the opportunity for the cassette material to become pinched or positioned between the elements during operation. The piston 40 may be manufactured from a lubricated material such as acetel fluoropolymer (for example, Delrin AF from DuPont, Co., Wilmington, Del.), and the base 50 from a glass reinforced polycarbonate (for example, a 10% glass material Lexan 500 from GE Plastics, Pittsfield, Mass.), to permit largely unrestricted motion of the piston 40 relative to the base 50 despite the potential for repeated contact between two elements. The number of splines 44 and ribs 54 should be such that the space 45 between each spline 44 and the space 55 between each rib 54 (such being substantially equivalent if the thickness of each spline 44 is substantially equivalent to the thickness of each rib 54) is of such a distance to enable the adjacent splines (or ribs as the case may be) to support the cassette 20 across the spaces 45, 55.

The complementary shaping of the piston 40 and the base 50 enables a resting cassette pumping chamber 30 to be supported by a constant surface area throughout an entire stroke of the piston 40, thereby foreclosing the opportunity for the cassette material to be stretched, unsupported or pinched during movement of the piston 40. Furthermore, the geometric relation between the elements permits a mathematical relation to be established. In the preferred embodiment, for example, the diameter of the piston 40 linearly decreases, relative to the interior of the pumping chamber 30, with the retraction of piston 40. A similar relation exists for the advancement of piston 40. Thus, during retraction of the piston 40, an enclosed volume is created which increases as a quadratic function of the piston's 40 movement. The benefit of such relation can be seen in the context of maintaining a constant fluid flow rate—the rate of piston movement can be controlled to achieve a predetermined flow rate.

Although the preferred embodiment defines a base 50 having a parabolic-like receiving surface 58 with a 45 degree angular displacement along the plurality of ribs 54, the angular displacement may measure from 30 to 60 degrees. Notwithstanding, the preferred embodiment ensures (i) a relatively significant pumping chamber volume, (ii) full support of the cassette pumping chamber 30 through an entire pumping stroke, and (iii) avoidance of trapped air within the pumping chamber 30.

Figure 8:
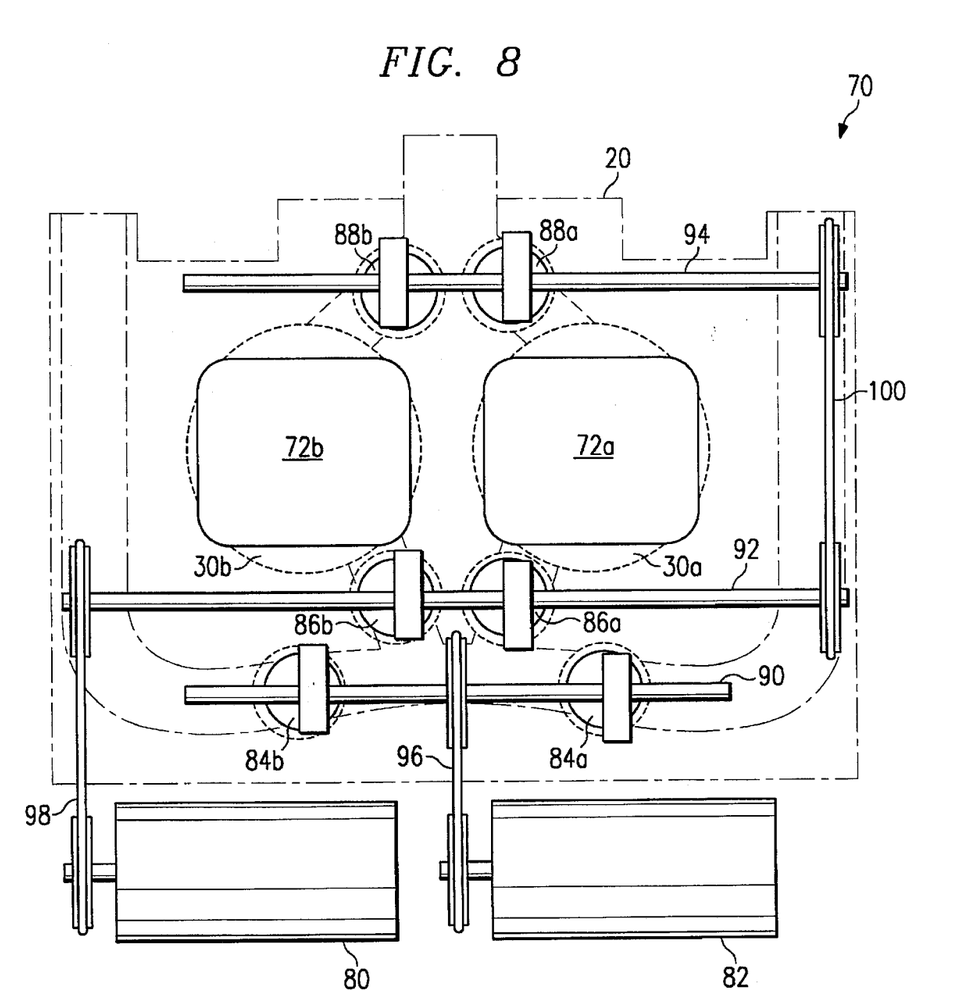
FIG. 8 is a view from beneath a pump mechanism which accommodates the disposable fluid cassette of FIG. 2.

FIG. 8 further illustrates the elements of the pumping mechanism 70 which accommodates the cassette 20 of FIG. 2 (an outline of the cassette 20 is provided). The pumping mechanism 70 incorporates a pair of stepper motors, or pumping motors 72a, 72b. The pumping motors 72a, 72b rotationally engage, through attached lead screws 43a, 43b, a threaded portion 41a, 41b of each piston 40a, 40b (see FIG. 1). Two drive motors 80, 82 control the operation of the mechanism's valves. Drive motor 80 engages cam shaft 92 (such driving inlet valves 86a and 86b) through a timing belt 98. Drive motor 80 also engages cam shaft 94 (such driving outlet valves 88a and 88b) through a timing belt 100 which rotationally couples cam shafts 92 and 94. Drive motor 82 engages cam shaft 90 (which drives inlet valves 84a and 84b) through an independent timing belt 96.

Referring to both FIG. 2 and 8, the interrelation of the pumping mechanism 70 and the fluid mixing operation are better illustrated. In short, mixing of a first and a second fluid, for the purposes of the illustrated embodiment, is accomplished through the continuous introduction of a first and a second fluid into multiple pumping chambers in a predefined, systematic pattern. The pumping mechanism 70, through the operation of a series of valves, controls the flow of fluid throughout the cassette 20. Specifically, a valve, if actuated, presses the first and second sheets of the cassette 20 together at a cassette valve location to occlude the valve location's corresponding flow path.

For pumping mechanism 70, inlet valves 84a, 84b, 86a, 86b control the introduction of fluid into the pumping chambers 30a, 30b. The inlet valves 84a, 84b, 86a, 86b act on the cassette 20 at valve locations 34a, 34b, 36a and 36b, respectively. Outlet valves 88a, 88b control the flow of fluid from the pumping chambers 30a, 30b by acting on cassette valve locations 38a, 38b. As an example, in preparation of filling pumping chamber 30b, valve 86a (valve location 38a) is actuated to close inlet flow path 28a, while valve 88b (valve location 38b) also occludes outlet path 32b to permit the accumulation of fluid within the pumping chamber 30b. During filling, valves 84a, 84b and 86b (valve locations 34a, 34b and 36b, respectively) open and close in a predetermined synchronized pattern to permit a ratio of the first and second fluids to enter the pumping chamber 30b. Upon completion of the fill, valves 86b and 88a respectively occlude flow paths 28b and 32a, and valve 88b is de-actuated to permit fluid to flow from the pumping chamber 30b. Fluid movement, whether filling or being expelled from the pumping chambers 30a, 30b, is initiated through the movement of the mechanism's pump assemblies 10a, 10b.

Referring to FIG. 1 and the operation of the pump mechanism 70, a fastened retaining door 74 tightly constrains the cassette 20 against the upper surface of the pump mechanism. The retaining door 74 possesses a number of cavities 76a, 76b, such number corresponding to the number of pump assemblies included within the pump mechanism 70. The cavities 76a, 76b are complementary of and can fully receive at least a portion of the pistons 40a, 40b when such are in a fully advanced position. Accordingly, the conformance of the cavities 76a, 76b to the shaping of the pistons 40a, 40b enables the expulsion of substantially all the fluid from the pump chambers 30a, 30b for a full piston stroke. Complete fluid displacement makes such pumping mechanism 70 and its methodology suitable for single pumping stroke applications.

When the cassette 20 is operatively positioned in the pump mechanism 70, the cassette pumping chambers 30a, 30b align with and rest upon the pump assemblies 10a, 10b. The retaining door 74 effectively constrains the cassette 20 during operation. The formed volume of the paths and chambers of the cassette 20 may be slightly greater or less than the nominal constraining volume defined by the rigid constituents of the pump mechanism 70. Practically, the firm restraints of the pump mechanism 70 permit the development of relatively high fluid pressures within the cassette 20 without significant or detrimental deformation of the cassette material. Indeed, constraining the cassette 20 over effectively the entire cassette surface creates an inherently non-compliant system. Such non-compliance contributes to the ability of the pump mechanism 70 to produce consistent, accurate volumetric fluid delivery.

In the preferred embodiment, the cassette pumping chambers 30a, 30b do not rest directly upon the supporting surfaces of the piston 40 and/or base 50. Instead, a resilient material 78, attached about the upper portion of the base 50, operates to conform to the supporting surface of the piston assembly 10 without regard to whether the piston 40 is fully advanced, retracted or in some intermediate position. The resilient material 78 protects the pump mechanism 70 from fluid intrusion in the event any liquid is spilled on the device operational environment. The resilient material 78 also acts to further protect the cassette 20 from damage that could inadvertently occur through the operation and movement of the piston assembly 10.

In an alternative embodiment, the resilient material 78 could include reinforcement means to provide additional rigidity to the resilient material 78. As an example, reinforcement means could include a fine metal mesh or cloth embedded within the material used to fabricate the resilient material 78. Alternatively, the resilient material 78 could include a spiral wire which is capable of concentric expansion to provide facial and lateral support for a resting cassette 20 about the interior of the base 50 (when piston 40 is in a retracted position) or about the piston 40 (when piston 40 is in an advanced position). Lastly, the material 78 could be formed of cloth altogether to eliminate any elasticity. This alternative embodiment, and its variations, could permit the use of fewer rib/splines or provide greater reliability in applications that require the piston assembly 70 to operate in larger applications, in the presence of greater fluid pressures or both.

Figure 10:
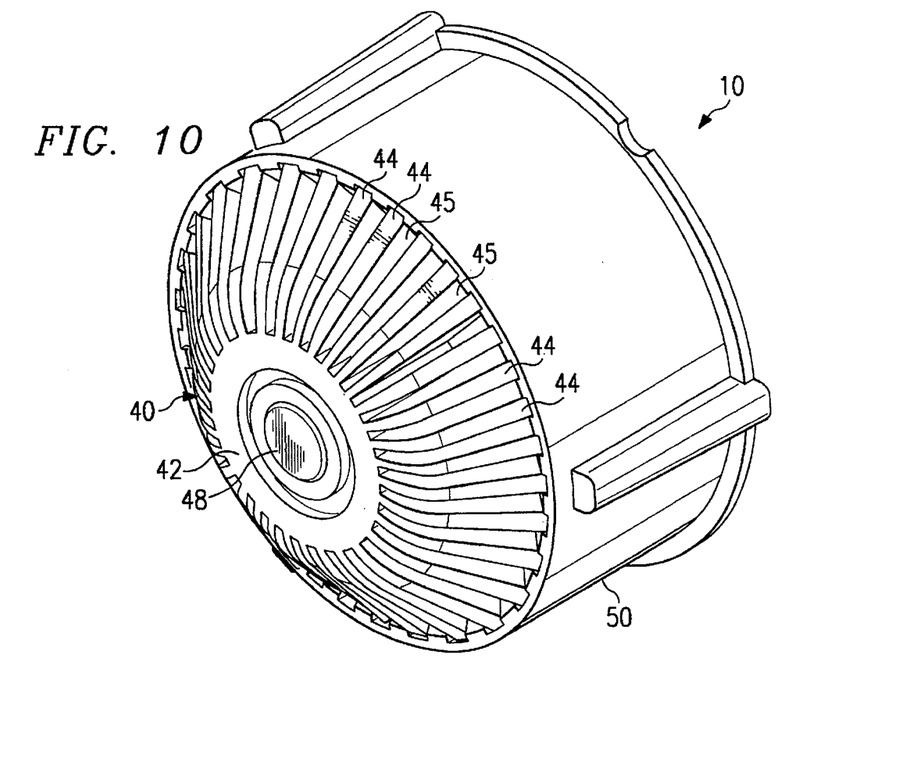
FIG. 10 is a perspective view of the piston assembly in a fully advanced state.

Returning to FIG. 1, piston 40a is fully retracted (see also FIG. 9) and piston 40b is fully advanced (see also FIG. 10). Relative to fluid displacement, pump chamber 30a would be substantially full of fluid, and pump chamber 30b would have just expelled its contents. For the present embodiment, the pump mechanism 70 can deliver substantially continuous fluid flow through the sequential filling and expulsion of fluid from the pumping chambers 30a, 30b.

In addition to providing substantially continuous flow, the pump mechanism 70 of the present embodiment incorporates a four-step filling protocol, which is in parallel to the expulsion of fluid from the other pump chamber, to ensure the volumetric accuracy of the delivered fluid. First, valve 88a is actuated and a first fluid is introduced into the pumping chamber 30a through the synchronized operation of the inlet valves. The pump motor 72a retracts a predefined amount to admit a volumetric quantity of the first fluid that, relative to the total volume of the pumping chamber 30a, satisfies a predefined fluid mixture ratio. Second, the system tests the volumetric accuracy of the first fluid within the pump chamber 30a. As a prelude to performing the test, valve 86a is actuated to occlude inlet path 28a. The pump motor 72a is advanced a few steps to increase the pressure within the pumping chamber 30a to a predetermined level. Based upon both the relative position of the piston 40a and the measured chamber pressure, the fluid delivery system determines: (i) whether the proper quantity of fluid was delivered to the pumping chamber 30a; (ii) whether air is present within the pumping chamber 30a (wherein air is more compliant than the pumped fluids); and (iii) the functionality of valves 86a and 88a. Third, a second fluid is introduced into the pumping chamber 30a through the synchronized operation of the inlet valves. Lastly, the accuracy of the total fluid volume is tested in accordance with the procedure above. Upon determining that the pump chamber has filled properly, the fill protocol is completed.

As should be gained from this operational description, the piston assembly 10 reduces the opportunity for damage to blood or blood-fluid mixtures in the pumping process. Specifically, the pump assembly 10 does not possess those features that (i) facilitate the trapping of blood in or about the pumping chamber 30 or (ii) subject the blood to damaging compressive forces (roller pumps) or shearing forces (centrifugal pumps).

From the relationship correlating piston position to pumping chamber volume, one will appreciate that various fluids may be mixed at definable ratios through simply controlling the number of steps the pumping motors 72a, 72b move for each fill stage. As well, the total volumetric flow rate delivered by the pump mechanism 70 is dependent upon the user-defined, cycle interval.

It should be understood by one skilled in the art that the pump mechanism 70 disclosed is one embodiment, and the piston assembly 10 of the present invention is not unique to or dependent upon any one embodiment. Moreover, the piston assembly 10 of the present invention may be used in various other pump mechanisms, utilizing differing fluid fill and expulsion protocols, fluid delivery systems or implemented in other fields of use without departing from the scope of the invention.

In an alternative embodiment, the piston 40 has a base plate to which extends upwardly therefrom a plurality of fins. The fins are parallel to each other, and transversely extend across the base plate. The upper surface of the fins generally assumes the form of a convex supporting surface. The base 50 includes a collar and a plurality of ribs. Each of the ribs are parallel to another and transverse the interior of the collar. The upper surface of the plurality of ribs generally assumes the form of a concave receiving surface. Further, the plurality of ribs are spaced to accommodate the movable interposition of the plurality of fins. The concave receiving surface of the base 50 inversely complements the convex supporting surface of the piston 40. The base 50 receives the piston 40 through the lowermost opening of the collar, opposite of the concave receiving surface. In operation, when the piston 40 is fully advanced, the base plate of the piston would be adjacent to or contacting the lowermost edge of the collar, such edge being that which surrounds the lowermost opening thereof.

It should be understood by one skilled in the art that the circular shape of the piston assembly 10 is but one embodiment, wherein the piston assembly 10 may assume a limitless variety of geometric shapes (e.g., ellipses, rectangular) and sizes.

While the invention has been described herein relative to a number of particularized embodiments, it is understood that modifications of and alternatives to, these embodiments, such modifications and alternatives obtaining the advantages and benefits of this invention, will be apparent to those of ordinary skill in the art having reference to this specification and its drawings. It is contemplated that such modifications and alternatives are within the scope of this invention as subsequently claimed herein, and it is intended that the scope of the invention disclosed herein be limited only by the broadest interpretation of the appended claims to which the inventors are legally entitled.

We claim:

1. A piston assembly of a fluid pump mechanism comprising:

a convex member having a central shaft and a convex upper surface, such convex upper surface being defined by a plurality of splines which extend outward from the central shaft for a predefined distance; and a concave member having a collar a concave upper surface and a passage extending through the concave member, such concave upper surface being defined by a plurality of ribs which extend inwardly from the collar and terminate at a predefined location which defines the passage, wherein in an operational state the central shaft is movably received within the passage and the plurality of splines are movable interposed between the plurality of ribs.

2. The piston assembly of claim 1 further comprising a pressure sensor being fixedly positioned within the central shaft of the convex member.

3. The piston assembly of claim 1 wherein each rib and each spline has a thickness which is substantially equivalent.

4. The piston assembly of claim 1 wherein the convex upper surface has a first surface area and the concave upper surface has a second surface area, such first and second surface areas being substantially equivalent.

5. The piston assembly of claim 4 further comprises an operational surface area when the convex member is received by the concave member in the operational state, the operational surface area being generated by a varying intersection of the convex upper surface intersecting with the concave upper surface during movement of the convex member relative to the concave member, wherein the operational surface area remains constant throughout a full range of movement of the convex member and said operational surface area is substantially equivalent to the second surface area.

6. A piston assembly of a pump mechanism, comprising:
  (a) a piston having a cylindrical hub and a plurality of splines extending radially outward therefrom, each spline having a first height at the cylindrical hub and a lesser height at a perimeter of the piston thereby creating a first angular displacement along each spline; and
  (b) a base having a cylindrical collar with a plurality of ribs extending radially inward toward a longitudinal axis of the collar, wherein the plurality of ribs terminate at a point short of the longitudinal axis by a predefined distance thereby creating a passage extending through the base, each rib having a first height at the cylindrical collar and a lesser height at the point where each rib terminates, thereby creating a second angular displacement along each rib, wherein,
the passage of the base operatively receives the cylindrical hub of the piston and the plurality of splines are operatively interposed between the plurality of ribs.

7. The piston assembly of claim 6 wherein the first and second angular displacements for the plurality of splines and ribs, respectively, are equivalent and may range from 30 to 60 degrees.

8. The piston assembly of claim 6 wherein the plurality of ribs substantially assume a concave shape having a first surface area and the plurality of splines assume a convex shape having a complementary second surface area, wherein the first surface area and second surface area are equivalent.

9. The piston assembly of claim 8 wherein during advancement and retraction of the piston relative to the base, an operational surface area is created along a variable interrelation of the first and second surface areas, wherein the operational surface area remains constant and is substantially equivalent to either of the first or second surface areas.

10. The piston assembly of claim 6 wherein a maximum volume of the pumping assembly is determined by the base dimensions.

11. The piston assembly of claim 6 further comprising a pressure sensor positioned in the hub cylinder.

12. A piston assembly of a pump mechanism comprising:
  (a) a base having a cylindrical collar with a cylindrical bore and a concave upper surface, the concave upper surface being defined by a plurality of ribs that transverse the bore, each rib being parallel to another; and
  (b) a piston having a base means and a convex upper surface, the convex upper surface being defined by a plurality of splines that extend upward from the base means, each spline being parallel to another and spaced to be operatively received between the plurality of ribs.

13. A pump mechanism, comprising:
  a fluid inlet;
  a fluid outlet; and
  at least one fluid pumping chamber, positioned between and in fluid communication with the fluid inlet and the fluid outlet, each fluid pumping chamber including:
    a convex member having a central shaft and a convex upper surface, such convex upper surface being defined by a plurality of splines which extend outward from the central shaft for a predefined distance; and
    a concave member having a collar, a concave upper surface and a passage extending through the concave member, such concave upper surface being defined by a plurality of ribs which extend inwardly from the collar and terminate at a predefined location which defines the passage, wherein in the central shaft is movably received within the passage and the plurality of splines are movable interposed between the plurality of ribs.

14. The pump assembly of claim 13 further comprising a pressure sensor being fixedly posited within the central shaft of the convex member.

15. The pump mechanism of claim 13 wherein each rib and each spline has a thickness which is substantially equivalent.

16. The pump mechanism of claim 13 wherein a maximum volume of the fluid pumping chamber is determined by the concave member and its dimensions.

17. The pump mechanism of claim 13 wherein each pumping fluid chamber further includes a fixed retention means, which contacts the collar of the concave member, having a cavity which complements, and is capable of receiving, the convex member.

18. The pump mechanism of claim 13 wherein the convex upper surface has a first surface area and the concave upper surface has a second surface area, such first and second surface areas being substantially equal.

19. The pump mechanism of claim 18 wherein the convex member and concave member operationally interrelate to define an operational surface area, the operational surface area being generated by a varying intersection of the concave upper surface intersecting the concave upper surface during movement of the convex member relative to the concave member.

20. The pump mechanism of claim 19 wherein the operational surface area remains constant throughout a full range of movement of the convex member relative to the concave member and said operational surface area is substantially equivalent to the second surface area.

* * * * *